(12) United States Patent
Anderson

(10) Patent No.: US 8,491,544 B2
(45) Date of Patent: Jul. 23, 2013

(54) ENTERAL FEEDING CONNECTOR

(75) Inventor: Kelly M. Anderson, St. Louis, MO (US)

(73) Assignee: Covidien LP, Mansfield, MA (US)

( * ) Notice: Subject to any disclaimer, the term of this patent is extended or adjusted under 35 U.S.C. 154(b) by 438 days.

(21) Appl. No.: 12/818,372

(22) Filed: Jun. 18, 2010

(65) Prior Publication Data

US 2011/0313369 A1 Dec. 22, 2011

(51) Int. Cl.
*A61M 5/14* (2006.01)

(52) U.S. Cl.
USPC .......................... 604/256; 604/910; 128/912

(58) Field of Classification Search
USPC .................. 604/910, 256; 128/912; 251/93, 251/89.5, 149.9
See application file for complete search history.

(56) References Cited

U.S. PATENT DOCUMENTS

| | | |
|---|---|---|
| 4,326,516 A | 4/1982 | Schultz et al. |
| 4,354,490 A | 10/1982 | Rogers |
| 4,631,056 A | 12/1986 | Dye |
| 4,752,292 A | 6/1988 | Lopez et al. |
| 5,137,524 A | 8/1992 | Lynn et al. |
| 5,344,414 A | 9/1994 | Lopez et al. |
| 5,520,665 A * | 5/1996 | Fleetwood .................... 604/537 |
| 6,077,259 A | 6/2000 | Caizza et al. |
| 6,423,053 B1 | 7/2002 | Lee |
| 6,981,977 B2 | 1/2006 | Herweck et al. |
| 2007/0106265 A1 | 5/2007 | Gillis |

* cited by examiner

*Primary Examiner* — Kevin C Sirmons
*Assistant Examiner* — Deanna K Hall

(57) ABSTRACT

A female enteral feeding connector includes a body having a hollow interior and an opening extending into the hollow interior for receiving a tip of a preselected male enteral feeding connector. A deformable retainer is mounted in the hollow interior adjacent the opening. A guard is mounted in the hollow interior and spaced from the retainer. A stop is positioned in the hollow interior for obstructing the opening in the body. The stop is moveable through the deformable retainer by application of a manual force on the preselected male enteral feeding connector from an obstructing position in which the stop obstructs the opening in the body from receiving the tip of the preselected male enteral feeding connector, to a non-obstructing position in which the stop permits the opening in the body to receive the tip of the preselected male enteral feeding connector.

19 Claims, 5 Drawing Sheets

ENTERAL FEEDING CONNECTOR

FIELD OF INVENTION

The present invention generally relates to an enteral feeding tube, and more particularly to an enteral feeding tube having a discriminating connector.

BACKGROUND

Feeding tube and catheter misconnections are a serious problem in hospitals. One such type of misconnection error involves enteral feeding tubes and intravenous catheters. Enteral feeding tubes are used to administer liquid nutritional solutions and medications directly to a patient's gastrointestinal system. In contrast, intravenous catheters are used to administer liquid nutritional solutions and medications directly to a patient's vascular system. Patients may be harmed if feeding solutions are administered intravenously and vice versa. Errors such as this occur because medical professionals use similar or identical tubing for different purposes. The use of luer tips, including luer-lock components, contributes to many of these errors because they enable functionally dissimilar tubes or catheters to be connected. For example, a luer tip may be inserted improperly into a connector or adaptor of a feeding tube, with potential harmful results. The present invention is directed a discriminating connector assembly for ensuring that the proper tubing and catheters are connected.

SUMMARY

In one aspect of the present invention, a female enteral feeding connector for connecting a feeding tube to a preselected male enteral feeding connector having a tip of a predetermined width and length generally comprises a body having a hollow interior and an opening extending into the hollow interior sized and shaped for receiving the tip of the preselected male enteral feeding connector. The body is adapted to be connected to a feeding tube. A deformable retainer is mounted in the hollow interior of the body adjacent the opening. A guard is mounted in the hollow interior of the body spaced from the retainer. A stop is positioned in the hollow interior of the body for obstructing the opening in the body except when the tip of the preselected male enteral feeding connector is inserted into the connector body opening. The stop is moveable through the deformable retainer by application of a manual force on the preselected male enteral feeding connector from an obstructing position located between the opening and the retainer, in which the stop obstructs the opening in the body from receiving the tip of the preselected male enteral feeding connector, to a non-obstructing position located between the retainer and the guard, in which the stop permits the opening in the body to receive the tip of the preselected male enteral feeding connector.

In another aspect, a female enteral feeding connector for connecting a feeding tube to a preselected male enteral feeding connector having a tip of a predetermined width and length generally comprises a body having a hollow interior and an opening extending into the hollow interior sized and shaped for receiving the tip of the preselected male enteral feeding connector. The body is adapted to be connected to a feeding tube. A stop is positioned in the body for obstructing the opening in the body except when the tip of the preselected male enteral feeding connector is inserted into the connector body opening. A retainer is adapted for retaining the stop in a position in which it obstructs the opening in the body. The retainer permits the stop to move away from the opening when engaged by the tip of the preselected male enteral feeding connector to permit insertion of the tip into the opening.

BRIEF DESCRIPTION OF THE DRAWINGS

Corresponding reference characters indicate corresponding parts throughout the drawings.

DETAILED DESCRIPTION OF THE DRAWINGS

Figure 1:
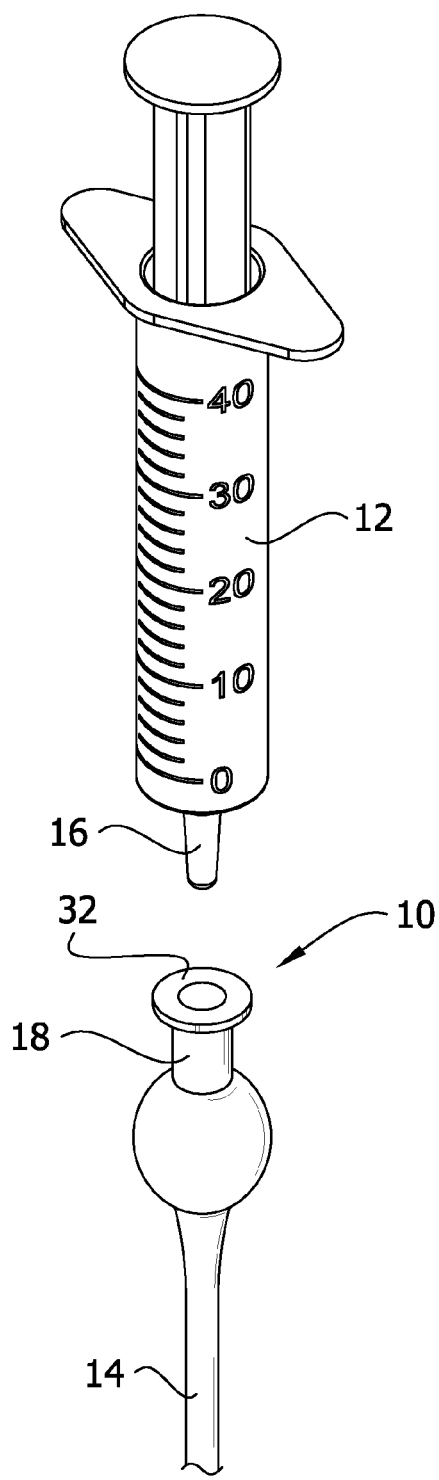
FIG. 1 is a perspective of a syringe and a portion of a feeding tube having a connector assembly of the present invention attached thereto.
Figure 2:
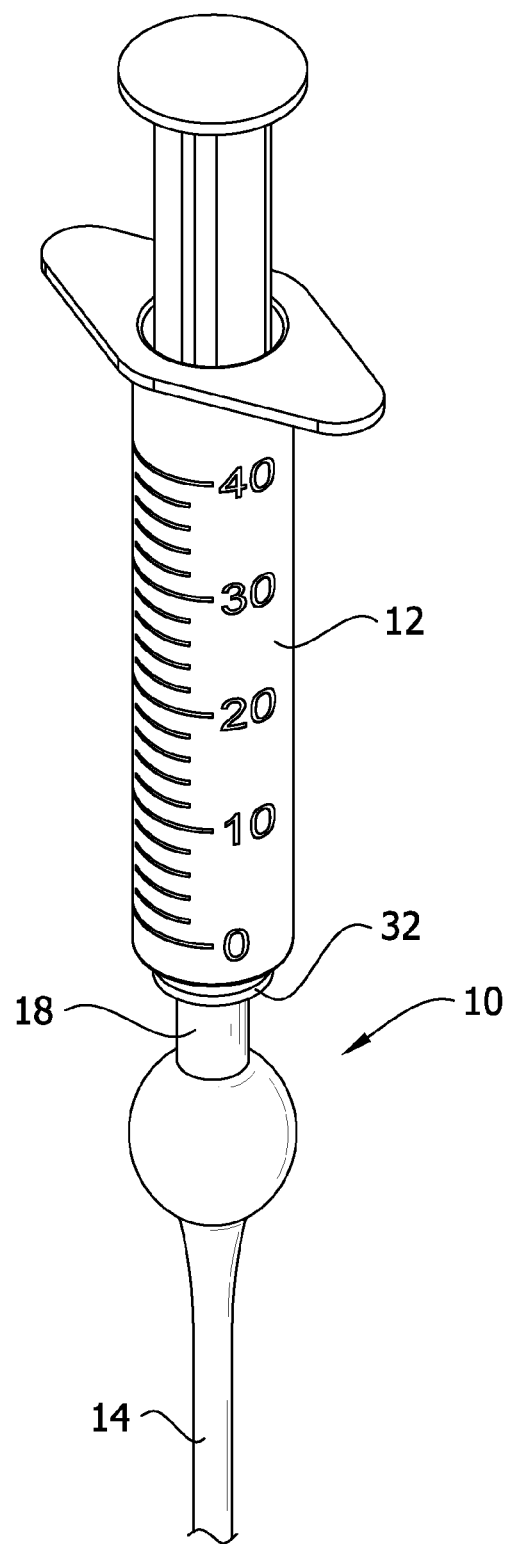
FIG. 2 is a perspective of the syringe and feeding tube connected by the connector assembly.

Referring to FIGS. 1 and 2, the present invention is directed to an enteral feeding tube connector assembly, generally indicated at 10, configured to provide a sealed fluid connection between a syringe 12 and an enteral feeding tube 14. The connector assembly 10 comprises a tip 16 (broadly, a male connector) attached to the syringe 12, and a fitting 18 (broadly, a female connector) attached to the feeding tube 14. As will be explained in greater detail below, the connectors are preselected such that the fitting 18 is adapted to receive the tip 16 to provide the sealed connection between the syringe 12 and the feeding tube 14 so nutrients can be delivered from the syringe through the feeding tube to a patient. It is understood the tip 16 could be attached to a feeding tube (not shown) for connecting two feeding tubes together. The tip 16 and fitting 18 may be formed from a rigid plastic, such as polypropylene. Alternatively, the tip 16 and fitting 18 may be formed from another material.

Figure 3:
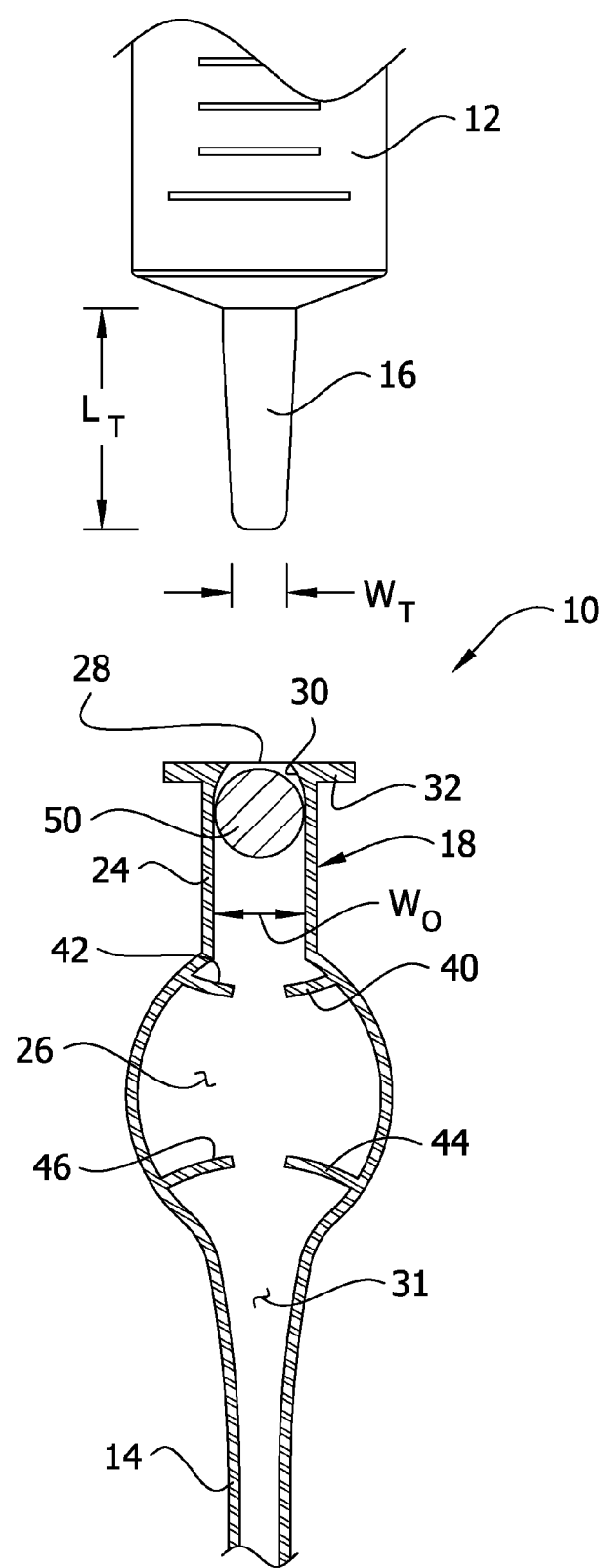
FIG. 3 is a partial elevation of the syringe and tip of the connector assembly, and a cross section of the feeding tube and fitting of the connector assembly separated from the syringe.

In the illustrated embodiment, the tip 16 is integrally formed with the syringe 12 by molding. The tip 16 tappers to a predetermined width WT over a length LT (FIG. 3). The fitting 18 comprises a body 24 integrally formed with an end of the feeding tube 14 such as by molding. It is understood that either the tip 16 or the fitting 18 can be formed separately from the syringe 12 or feeding tube 14, respectively, and attached thereto by a suitable means. The body 24 has a hollow interior 26 and an opening 28 extending into the hollow interior. The body 24 has a generally tubular shape so the opening 28 has a circular cross section. A width WO of the opening 28 is sized for receiving the tip 16 of the syringe 12. The body 24 has a tapered inner surface 30 surrounding the opening 28 for engaging an outer surface of the tip 16. The inner surface 30 narrows toward the opening 28 to seal around the tip 16 for connecting the syringe 12 to the fitting 18. The body 24 may have other shapes without departing from the scope of the present invention. The body 24 may also be provided with an o-ring (not shown) for sealing the connector assembly 10 between the tip 16 and fitting 18. The hollow interior 26 of the body 24 includes a port 31 opposite the opening 28 for communicating the hollow interior with the feeding tube 14. A flange 32 is disposed around the opening 28 to strengthen and reduce the flexibility of the opening.

Referring to FIG. 3, a deformable retainer 40 mounted in the hollow interior 26 of the body 24 adjacent the opening 28 is generally coaxially aligned with the opening. The retainer 40 comprises an annular member having a tapered inner surface 42. In one embodiment, the inner surface tapers away from the opening 28 so that it is broadest at a portion of the retainer 40 that is closest to the opening and narrowest at a portion of the retainer that is farthest from the opening. The retainer 40 may have other configurations without departing from the scope of the present invention.

A guard 44 is also mounted in the hollow interior 26 of the body 24. The guard 42 is spaced from the retainer 40 and located adjacent the port 31 so that the guard surrounds the port. The guard 44 comprises an annular member having a tapered surface 46 facing the hollow interior 26 of the body 24. The tapered surface 46 tapers toward the retainer 40 so that it is broadest at a portion of the guard 44 that is closest to the port 31 and narrowest at a portion of the guard that is closest to the retainer. The guard 44 may have other configurations without departing from the scope of the present invention. A stop 50 is positioned in the hollow interior 26 of the body 24 for obstructing the opening 28. In the illustrated embodiment the stop 50 comprises a spherical member. However, the stop may have other shapes and configurations without departing from the scope of the present invention.

Figure 4:
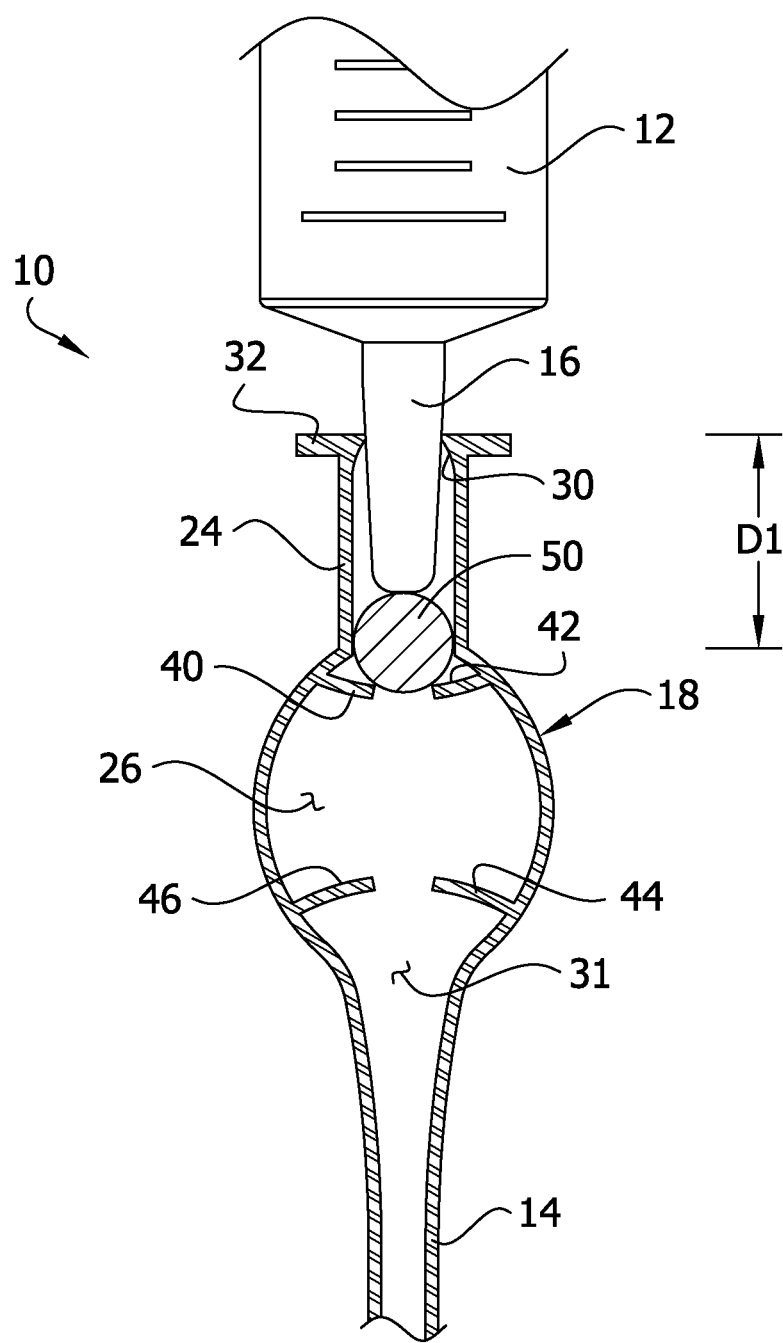
FIG. 4 is a view similar to FIG. 3 but showing the syringe and tip partially inserted into the fitting of the connector assembly.
Figure 5:
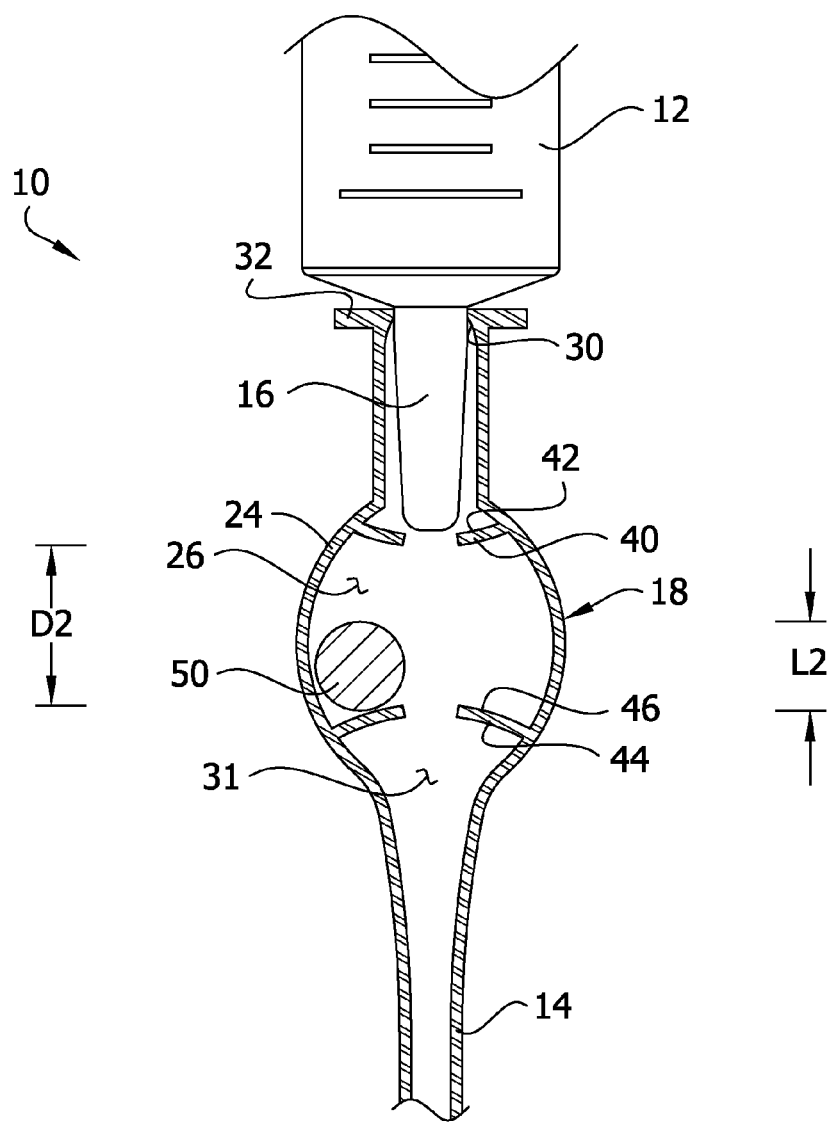
FIG. 5 is a view similar to FIGS. 3 and 4 but showing the syringe and tip fully inserted.

Prior to inserting the tip 16 into the opening 28, the stop 50 is retained in the opening by the retainer 40, obstructing the opening. When the tip 16 is inserted into the opening 28, the tip engages the stop 50, pressing the stop against the inner surface 42 of the retainer 40 (FIG. 4). The retainer 40 is spaced from the opening 28 by a distance D1 that is less than a combined length $L_C$ of the tip 16 and the stop 50 so that if the tip is inserted with a sufficient force, the stop 50 will deform the retainer 40 by spreading open the narrow portion of the retainer, allowing the stop to move past the retainer. The guard 44 is spaced from the retainer 40 by a distance D2 that is greater than a length L2 of the stop 50 so that the stop 50 will then move farther into the hollow interior 26 of the body 24 between the retainer 40 and the guard 44, permitting the tip 16 to enter the interior of the body (FIG. 5). The stop 50 will finally come to rest on the tapered surface 46 of the guard 44. At this point the tip 16 may be fully inserted into the opening 28 attaching the tip to the fitting 18. The tapered surface 46 of the guard 44 is configured to hold the stop 50 away from the port 32 allowing nutrients from the syringe 12 to pass unobstructed through the port 32 and into the feeding tube 14.

The connector assembly 10 removes the opportunity for connection error during treatment of a patient because no device other than one having a mating connector can be connected to the feeding tube 14 without substantial leakage.

Having described the invention in detail, it will be apparent that modifications and variations are possible without departing from the scope of the invention defined in the appended claims.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A female enteral feeding connector for connecting a feeding tube to a preselected male enteral feeding connector having a tip a predetermined width and length, said female enteral feeding connector comprising:
   a body having a hollow interior and an opening extending into the hollow interior sized and shaped for receiving the tip of the preselected male enteral feeding connector, said body being adapted to be connected to a feeding tube;
   a stop positioned in the body for obstructing the opening in the body except when the tip of the preselected male enteral feeding connector is inserted into the connector body opening, the opening being free of structure other than the stop so the tip of the male enteral feeding connector directly engages the stop when the tip is inserted into the opening; and
   a retainer adapted for retaining the stop in a position in which it obstructs the opening in the body, said retainer permitting the stop to move away from the opening when the stop is engaged by the tip of the preselected male enteral feeding connector to permit insertion of the tip into the opening.

2. The connector as set forth in claim 1 wherein said retainer is spaced from the opening by a distance less than a combined length of the tip and the stop.

3. The connector as set forth in claim 1 wherein said retainer deforms to permit the stop to move away from the opening when engaged by the tip of the preselected male enteral feeding connector to permit insertion of the tip into the opening.

4. The connector as set forth in claim 1 further comprising a guard spaced from the retainer for preventing the stop from blocking flow through the hollow interior of the body between the tip of the male connector and the feeding tube when the stop moves away from the opening, wherein the guard is disposed adjacent an end of the connector that connects to the feeding tube and opposite an end of the connector that receives the tip of the male enteral feeding connector.

5. The connector as set forth in claim 4 wherein the guard is spaced from the retainer by a distance greater than a length of the stop.

6. The connector as set forth in claim 4 wherein:
   the body has a port communicating the hollow interior with the feeding tube; and
   the guard surrounds the port.

7. The connector as set forth in claim 6 wherein the guard has a tapered surface that is narrowest adjacent the retainer.

8. The connector as set forth in claim 1 wherein said body opening has a width at least as great as the width of the tip of the preselected male enteral feeding connector.

9. The connector as set forth in claim 1 wherein said body opening has a width less than that of the stop.

10. The connector as set forth in claim 9 wherein said body opening and the stop each have a circular cross section.

11. The connector as set forth in claim 1 wherein the retainer is generally coaxially aligned with the opening in the body.

12. The connector as set forth in claim 11 wherein the retainer has a tapered inner surface for engaging the stop.

13. The connector as set forth in claim 12 wherein the tapered inner surface of the retainer is broadest adjacent the opening.

14. The connector as set forth in claim 1 wherein the body has a tapered inner surface surrounding the opening.

15. The connector as set forth in claim 14 wherein the tapered inner surface of the body is narrowest adjacent the opening.

16. The connector as set forth in claim 15 further comprising a strengthening element positioned around the opening for reducing flexibility of the opening.

17. The connector as set forth in claim 16 wherein the strengthening element comprises a flange surrounding the opening.

18. The connector as set forth in claim 1 wherein upon removal of the tip of the preselected male enteral feeding connector from the opening after the tip has been fully inserted into the opening, the stop remains in a position away from the opening.

19. A female enteral feeding connector for connecting a feeding tube to a preselected male enteral feeding connector having a tip a predetermined width and length, said female enteral feeding connector comprising:
- a body having a hollow interior and an opening extending into the hollow interior sized and shaped for receiving the tip of the preselected male enteral feeding connector, said body being adapted to be connected to a feeding tube;
- a stop positioned in the body for obstructing the opening in the body except when the tip of the preselected male enteral feeding connector is inserted into the connector body opening; and
- a retainer adapted for retaining the stop in a position in which it obstructs the opening in the body, said retainer permitting the stop to move away from the opening past the retainer when engaged by the tip of the preselected male enteral feeding connector to permit insertion of the tip into the opening.

* * * * *